Figure 1:
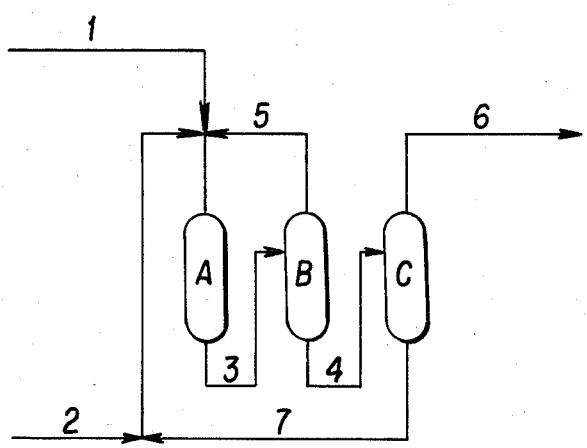

United States Patent [19]
Paparatto

[11] Patent Number: 4,808,759
[45] Date of Patent: Feb. 28, 1989

[54] PROCESS FOR THE CATALYTIC TRANS-HALOGENATION OF A POLY-IODO-BENZENE

[75] Inventor: Giuseppe Paparatto, Milan, Italy

[73] Assignee: Montedipe S.p.A., Milan, Italy

[21] Appl. No.: 81,798

[22] Filed: Aug. 5, 1987

[51] Int. Cl.$^4$ .................. C07C 17/158; C07C 21/24; C07C 25/02
[52] U.S. Cl. .................................. 570/202; 570/203; 570/204
[58] Field of Search ............... 560/182; 570/203, 204, 570/206, 208, 220, 202

[56] References Cited

FOREIGN PATENT DOCUMENTS

| 0183579 | 6/1986 | European Pat. Off. | 570/203 |
| 0077631 | 5/1982 | Japan | 570/203 |
| 2120328 | 6/1987 | Japan | 570/204 |
| 2120329 | 6/1987 | Japan | 570/204 |
| 0368215 | 11/1970 | U.S.S.R. | 570/204 |

Primary Examiner—Werren B. Lone
Attorney, Agent, or Firm—Stevens, Davis, Miller & Mosher

[57] ABSTRACT

The invention concerns a process for the catalytic trans-halogenation of a poly-iodo-benzene, wherein said poly-iodo-benzene is made to react with benzene and with oxygen, in the presence of a zeolite of the X type or of the Y type, exchanged with an alkali metal, with thallium or with a rare earth and anyway present in a form different from the acidic form.

12 Claims, 2 Drawing Sheets

PROCESS FOR THE CATALYTIC TRANS-HALOGENATION OF A POLY-IODO-BENZENE

BACKGROUND OF THE INVENTION

European Pat. Nos. 181790 and 183579, in the Applicant's name, disclose an oxy-iodination of benzene, mono-iodo-benzene and small amounts of di-iodo-benzene being thus formed; whilst the mono-iodo derivative can be advantageously used on an industrial scale, e.g. for the manufacture of phenol, the di-iodo-benzenes have not yet found a sufficiently wide application field.

The Applicant has surprisingly found that particular and suitable operative conditions allow the di-iodo-benzenes to be easily trans-halogenated into mono-iodo-benzene, in the presence of oxygen and of benzene, according to the reaction:

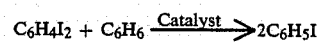

DISCLOSURE OF THE INVENTION

In its broadest aspect the invention relates to a process for the catalytic trans-halogenation of a poly-iodo-benzene and in particular of a di-iodo-benzene, characterized in that said poly-iodo-benzene is made to react with benzene and oxygen—or with other oxygen containing gas—in the presence of a zeolite of the X type or of the Y type, at least partially exchanged with an alkali metal, with thallium or with a rare earth and anyway present in a form different from the acidic form, i.e. from the H form, said zeolite being optionally admixed with an inert binder.

The above process can be very advantageously carried out in parallel to an oxyiodination of benzene, disclosed in the above European patents, which stated that undesired amounts are formed of di-iodo- (and poly-iodo-) benzenes; i.e. at the same time, and inside the same reaction zone, higher yields of mono-iodo-benzene can be obtained (as compared to the simple synthesis from $C_6H_6$ and iodine), because the undesired di-iodo-benzene byproducts can be recycled to the oxy-iodination reaction, thus supplying an additional source of iodine.

According to a preferred form of the invention, the space velocity is from 0.1 to 100 kg/hour of (poly-iodo-benzene+benzene) mixture per kg of pure zeolite (any binder excluded) and the di-iodo-benzenes (para-, ortho-, or meta-di-iodo-benzene, or their mixtures) are fed to the reaction as a solution in benzene.

One can use either a zeolite in the mono-alkali-metal form (e.g., in the sodium or potassium form) or a zeolites exchanged with two or more cations; it is possible e.g. to partially exchange the sodium of the sodium form with another cation e.g. with $K^+$ cation or with the cation of a rare earth. The same catalyst can be also prepared starting from the acidic form of zeolite, by first partially exchanging the proton with one of the desired cations (by using the solution of a water-soluble salt thereof) and subsequently neutralizing all of the residual acidic sites with a diluted NaOH, KOH, RbOH, or CsOH solution; by using this latter technique, a completely exchanged catalyst is obtained, and all of the Bronsted's acidic sites, responsible for the decay of the catalytic activity, are eliminated.

The trans-iodination can be carried out according to the most different ways, however always within the scope of the invention. According to a very advantageous form, the reaction temperature is from 250° to 450° C. The benzene/poly-iodo-benzene molar ratio is from 100 to 1, and preferably from 20 to 1; the poly-iodo-benzene:$O_2$ molar ratio is from 10 to 0.05 (preferably from 5 to 0.5) and the reaction is carried out over a fluidized bed or over a fixed bed of zeolitic catalyst. Further optional operative details are reported hereinafter.

A solution of di-iodo-benzenes in benzene (at a concentration from 0.5 to 50%, preferably from 5 to 20% by weight) is evaporated and admixed with oxygen or air, (oxygen is preventing iodine from being formed) and the mixture is fed to a fixed-bed reactor, loaded with the catalyst, an inert diluent, e.g. nitrogen, being optionally used. The products can be recovered by cooling the stream leaving the reactor and resorting to usual treatments. In the case of a distillation, benzene is distilled as the overhead fraction and can be recycled to the reactor. The total pressure is usually not much higher than atmospheric pressure: lower or higher pressures can however be used. The catalyst maintains its activity for a long time, in particular when the process is carried out, in the gas phase, at 250°-450° C.; when the catalytic activity decreases under the admissible level, a regeneration is started; said regeneration can be consisting of a heating in air, for some hours, at 300°-550° C. According to an alternative and very efficacious regeneration, a benzene stream, optionally admixed with air, or with other oxygen-containing gas, is made to flow over the exhausted catalyst at 300°-550° C.

Also the initial activation of the catalyst is an important step; in general, an activation in air at 450°-550° C. or the methods disclosed in European Pat. Nos. 168,978; 169,026; and 169,027 can be used.

Figure 2:
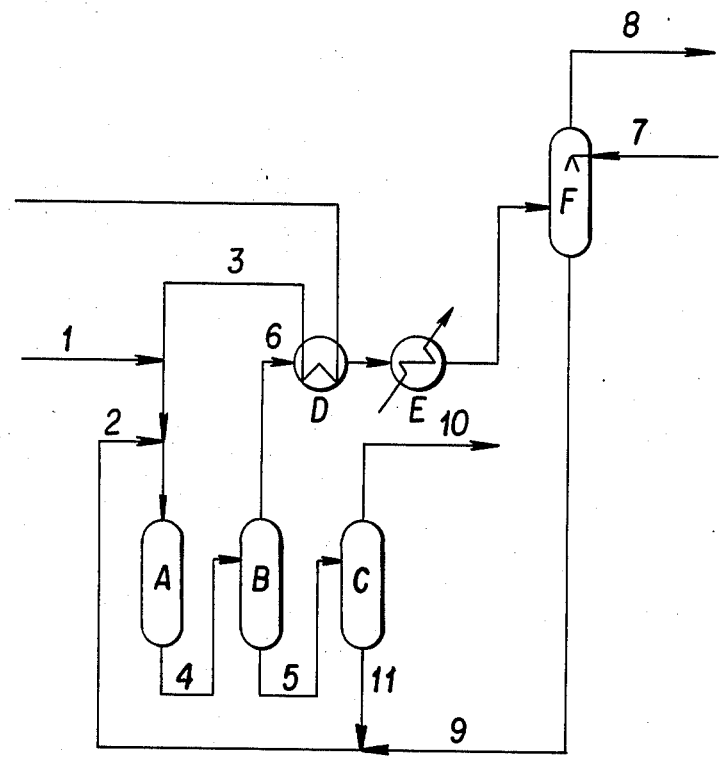

The invention is described also with the aid of the figures, which are however in no way limitative of the scope of the same invention:

FIG. 1 concerns a simple trans-halogenation;

FIG. 2 provides a parallel oxidative and catalytic mono-iodination of benzene with iodine.

Following the flow diagram of FIG. 1, benzene, admixed with oxygen (1) and a solution containing one or more di-iodo-benzenes (2) enter, in the gas phase, reactor (A), loaded with the catalyst; the raw reaction effluent (3) is cooled (inside heat exchangers and heat recovery units, not shown on the Figure) and transferred to separator B, from the bottom of which mono-iodo-benzene and residual di-iodo-benzenes are withdrawn (4), while the most part of unreacted benzene and oxygen (5) are recycled to the trans-halogenation reaction. Distillation tower C allows the fractionation of the halogenated compounds; iodo-benzene (6) leaves the tower as the overhead fraction and the residual di-iodo-benzenes (7), admixed with a portion of mono-iodo-benzene and with a small amount of benzene, are recycled to the reaction zone.

According to FIG. 2, a solution, containing iodine in an excess of benzene (1), and a solution containing one or more di-iodo-benzenes (2) enter, in the gas phase, reactor A, together with a pre-heated stream of air (or of other oxidating gas) (3); the raw effluent from the simultaneous reactions of iodination and trans-iodination (4) is cooled (inside facilities not shown on the Figure) and transferred to separator B, from the bottom of which one withdraws a solution containing iodo-benzene and residual di-iodo-benzenes, together with a small amount of benzene (5),—whilst the most part of unreacted benzene, admixed with nitrogen-enriched air (6), is cooled in the recovery unit D and in cooler E before entering the separation and benzene recovery tower F (two towers in series are preferable), where the scrubbin liquid (7) can be consisting of benzene, iodo-benzene, di-iodo-benzenes or their mixtures. The nitrogen-enriched air (8) can be vented (or transferred to other units and the excess benzene (9) is recycled. Distillation tower C allows the fractionation of the halogenated compounds; iodo-benzene (10) outflows as the overhead fraction, and the residual di-iodo-benzenes (11) leave the tower bottom as the tail products and are combined with recycle stream (9). All the iodine feed is thus completely used, the iodine dispersed in the undesired byproducts (poly-iodo-benzenes) being completely recovered (by means of trans-halogenation). The following Examples are illustrating the invention, without however being in any way limitative of the scope thereof.

EXAMPLE 1

(13 X zeolite)

One gram of 13 X zeolite, traded by Union Carbide, was admixed with 0.3 g of binder ($SiO_2$) and the whole mixture was activated in air for 2 hours at 540° C.; the resulting catalyst was loaded into a quartz microreactor, kept at 400° C. and continuously fed with a mixture, in the gas phase, of benzene, p-di-iodo-benzene (p-DIB) and air, with a benzene:p-DIB:air molar ratio of 20:1:20. The pressure was slightly higher that 760 mmHg and the weight hourly space velocity (WHSV) was 6 kg/h of (benzene+di-iodo-benzene) mixture per kg of pure zeolite (binder excluded). The reaction continued for 6 hours and the reaction products were collected by condensation; the conversion of p-DIB was 92% and the selectivity to iodo-benzene (based on converted p-DIB) was 99%.

EXAMPLE 2

Example 1 was repeated using a zeolite NaY (traded too by Union Carbide); after 6 reaction hours, the di-iodo-benzene conversion was 80% and the selectivity to iodo-benzene was higher than 99%.

EXAMPLE 3

Example 1 was repeated, but the feedstock was a mixture which contained 86% by weight of benzene, 12% by weight of iodine and 2% by weight of para-di-iodo-benzene; after 6 hours of reaction, the iodine conversion was 100% and the resulting reaction mixture was showing the following composition:
19.9% by weight iodo-benzene;
1.5% by weight (para- + ortho-) di-iodo-benzene;
78.6% by weight benzene.

In other terms, under these conditions 25% of di-iodo-benzene was trans-halogenated to iodo-benzene.

What I claim is:

1. A process for the manufacture of mono-iodo-benzene by a catalytic trans-halogenation of a poly-iodo-benzene, characterized in that said poly-iodo-benzene is reacted at 250° to 450° C. with benzene and oxygen or oxygen-containing gas, in the presence of a zeolite of the X or of the Y type, at least partially exchanged with an alkali metal, with thallium or with a rare earth.

2. A process according to claim 1, wherein the trans-halogenation takes place in parallel to an oxidative mono-iodination (minor proportions of poly-iodo-benzenes, in particular di-iodo-benzenes, being formed), said poly-iodo-benzenes being recycled, as an additional iodine source, to the reaction zone, where said trans-halogenation and said mono-iodination reactions take place simultaneously.

3. A process according to claim 1, wherein the benzene:poly-iodo-benzene molar ratio is from 100 to 1.

4. A process according to claim 1, wherein the poly-iodo-benzene:oxygen molar ratio is from 10 to 0.05.

5. A process according to claim 1, wherein the space velocity is from 0.1 to 100 kg/h of (poly-iodo-benzene+benzene) mixture per kg of pure zeolite, any binder excluded.

6. A process according to claim 1, wherein the poly-iodo-benzene is fed as a solution in benzene, at a concentration from 0.5 to 50% by weight.

7. A process as defined in claim 6, wherein the said concentration is from 0.5 to 20% by weight.

8. A process for the manufacture of mono-iodo-benzene by catalytic trans-halogenation of a di-iodo-benzene, wherein said di-iodo-benzene is made to react at 250°–450° C. with air or with other oxygen-containing gas, in the presence of a zeolite of the X type or of the Y type, at least partially exchanged with an alkali metal (and anyway in a form different from the acidic form), according to benzene:di-iodo-benzene molar ratios from 20 to 1, according to di-iodo-benzene:$O_2$ molar ratios from 5 to 0.5 and at space velocities from 0.1 to 100 kg/hour of (poly-iodo-benzene+benzene) mixture per kg of pure zeolite.

9. A process according to claim 8, wherein the reaction is performed in a fluidized bed of catalyst.

10. A process according to claim 8, wherein the reaction is performed over a fixed bed of catalyst.

11. A process according to claim 8, wherein the catalyst is regenerated at 300°–550° C., by means of a benzene stream, optionally admixed with air or with other oxygen-containing gas.

12. A process as defined in claim 1, wherein the poly-iodo-benzene is di-iodo-benzene.

* * * * *

UNITED STATES PATENT AND TRADEMARK OFFICE
CERTIFICATE OF CORRECTION

PATENT NO. : 4,808,759

DATED : February 28, 1989

INVENTOR(S) : Giuseppe PAPARATTO

It is certified that error appears in the above-identified patent and that said Letters Patent is hereby corrected as shown below:

In the heading of the patent, between items [22] and [51], insert:

--[30] Foreign application priority data
August 11, 1986 [IT]   21465 A/86

Signed and Sealed this

Eighth Day of May, 1990

Attest:

HARRY F. MANBECK, JR.

*Attesting Officer*    Commissioner of Patents and Trademarks